(12) United States Patent
Klotz et al.

(10) Patent No.: US 6,461,039 B1
(45) Date of Patent: Oct. 8, 2002

(54) C-ARM X-RAY DEVICE

(75) Inventors: Erhard Paul Artur Klotz, Neumuenster; Hermann Schomberg, Hamburg, both of (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/680,190

(22) Filed: Oct. 5, 2000

(30) Foreign Application Priority Data

Oct. 5, 1999 (DE) ........................................ 199 47 809

(51) Int. Cl.$^7$ ................................................. H05G 1/02
(52) U.S. Cl. ........................................ 378/197; 378/196
(58) Field of Search ................................ 378/196, 197, 378/198

(56) References Cited

U.S. PATENT DOCUMENTS 4,653,083 A * 3/1987 Rossi ........................ 378/196
5,521,957 A * 5/1996 Hansen ...................... 378/198
6,113,264 A * 9/2000 Watanabe ................... 378/197
6,213,638 B1 * 4/2001 Rattner ...................... 378/198

FOREIGN PATENT DOCUMENTS

DE  19625407      1/1998    ............ A61B/6/02
EP   0763343 A1   3/1997    ............ A61B/6/00

* cited by examiner

*Primary Examiner*—Robert H. Kim
*Assistant Examiner*—Jurie Yun
(74) *Attorney, Agent, or Firm*—John Vodopia

(57) ABSTRACT

The invention relates to an X-ray device which includes a C-arm (12) carrying an X-ray source (2) and an X-ray detector (3), and includes a suspension device (14) with a joint (13), the X-ray source (2) and the X-ray detector (3) being rotatable about a propeller axis ($z_4$) which extends through the joint (13). In order to enable flexible movements in such an X-ray device, notably a wide variety of trajectories, according to the invention the X-ray device is construction in such a manner that the position of the propeller axis ($z_4$) can be changed in all spatial directions ($z_1$, $z_2$, $z_3$).

10 Claims, 5 Drawing Sheets

C-ARM X-RAY DEVICE

BACKGROUND OF THE INVENTION

The invention relates to an X-ray device which includes a C-arm carrying an X-ray source and an X-ray detector, and also includes a suspension device which carries the C-arm via a joint, the X-ray source and the X-ray detector being rotatable about a propeller axis which extends through the joint.

X-ray devices of this kind are generally known and are frequently used for medical diagnostic imaging. The patient to be examined is then usually positioned horizontally on a patient table. In order to form X-ray projections, notably for angiography, the projection direction can be varied within given limits. The X-ray source and the X-ray detector are thus rotatable in an angular range about the longitudinal axis of the patient; the angle between the projection direction and the longitudinal axis of the patient is adjustable and the suspension device carrying the C-arm is usually anchored in space in such a manner that it is rotatable in an angular range about a vertical axis. As a result, the X-ray source can occupy successive positions in time so as to describe given trajectories, for example, a semi-circular trajectory where the projection direction varies accordingly. Display in a fast succession of the projections thus obtained on a display screen offers the physician a better idea of the three-dimensional situation, for example of the vessels examined. Three-dimensional images of the volume examined can also be calculated from these projections.

In the known X-ray devices, however, the possibilities for adjustment and movement of the X-ray source are constrained by the mechanical construction of the X-ray device. For example, notably the position of the so-called propeller axis, i.e. the axis extending through the joint linking the C-arm to the suspension device, can change only in a horizontal plane extending through the patient. This constraint also limits the course of the trajectories that are possible. For example, in the known X-ray devices it is not possible for the X-ray source to describe a trajectory in the form of a full circle around the patient or in the form of two tilted full circles around the patient. To some extent this is also due to the fact that the joint linking the C-arm to the suspension device is not suitably designed, but essentially to the fact that the overall mechanism of the X-ray device, notably the weight of the C-arm, does not permit such motions.

Therefore, it is an object of the invention to provide an X-ray device which is mechanically stable and is capable of realizing different trajectories.

On the basis of an X-ray device of the kind set forth this object is achieved by means of an X-ray device.

SUMMARY OF THE INVENTION

The invention is based on the recognition of the fact that the trajectories that can be described in the known X-ray devices are also constrained by the fact that the position of the propeller axis can be changed in one plane only. Therefore, according to the invention the X-ray system, notably the C-arm, the joint and the suspension device are to be designed in such a manner that the position of the propeller axis can also be changed in other directions. When suitably constructed, the mechanism of the C-arm may also be simpler and notably the weight of the C-arm may be lower, so that the desired trajectories can be realized for the X-ray tube.

Further advantageous embodiments of the invention are disclosed in the further Claims.

Particularly advantageous is a further embodiment in which the suspension device and/or a holding device carrying the suspension device have a construction in the form of an arc of a circle. In this embodiment all axes of rotation of the X-ray device, notably also the propeller axis through the so-called isocenter in which the object to be examined is arranged and wherethrough the projection lines (the connecting line between X-ray source and X-ray detector) also extend, can be simply made to intersect. To this end, the suspension device or the holding device preferably exhibits the same curvature as the C-arm.

In a preferred embodiment of the invention the suspension device is constructed in such a manner that the C-arm and the joint are rotatable about a horizontal axis of rotation which extends perpendicularly to the propeller axis. As a result, in comparison with the known X-ray devices the C-arm can be constructed so as to be significantly simpler and above all lighter, because it need carry only the X-ray source and the X-ray detector but no further mechanical elements which enable the rotary motion about the axis of rotation in the known X-ray devices. This functionality is provided by the suspension device in this further embodiment.

Furthermore, the joint is constructed as a revolute joint in such a manner that the X-ray source and the X-ray detector can be rotated 360° around the axis of rotation an arbitrary number of times. This can be realized notably in the described further embodiment of the invention in which the C-arm can have a particularly light construction.

BRIEF DESCRIPTION OF THE DRAWINGS

The invention will be described in detail hereinafter with reference to the drawings. Therein.

DESCRIPTION OF THE PREFERRED EMBODIMENTS

Figure 1:
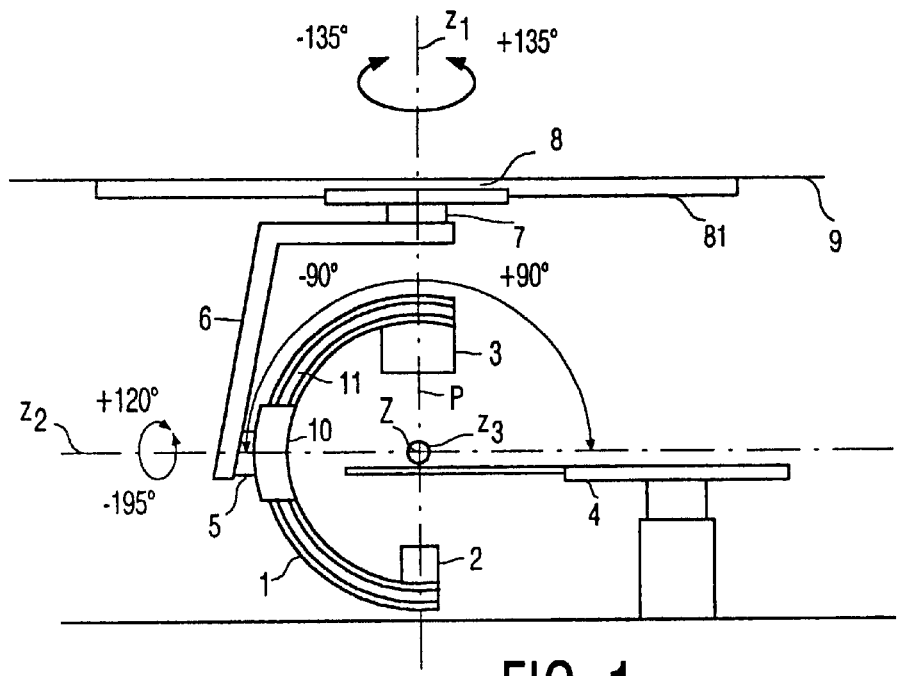
FIG. 1 shows a known X-ray system according to the state of the art.

The core of the known X-ray device shown in FIG. 1 is formed by a C-arm 1 whose ends carry a point-shaped X-ray source 2 and a flat X-ray detector 3, respectively. The C-arm is carried by a joint 5, that is, a so-called C-arm holder which itself is attached to a suspension device 6, that is, a so-called L-arm. The L-arm 6 is supported by a ceiling holder 7, that is, a so-called L-arm holder which itself is connected to the ceiling 9 or, as in the case shown, to a slide 8 suspended from ceiling rails 81. The ceiling holder 7 is constructed in such a manner that the L-arm 6 can be manually rotated about the vertical axis of rotation $z_1$ in an angular range of ±135°. The joint 5 is constructed in such a manner that the C-arm 1 can be rotated by motor in an angular range of from +120° to −195° about the horizontal axis $z_2$. Finally, the C-arm 1 can also be driven by motor about an axis of rotation $z_3$ which extends perpendicularly to both axes $z_1$, and $z_2$; to this end, the C-arm 1 is provided with suitable means, for example a holding device 10 which is connected to the joint 5 and is provided with a motor-driven gear wheel and a corresponding toothed rack 11. The three axes $z_1$, $z_2$, $z_3$ are chosen so that they intersect in one point, that is, the so-called isocenter Z in which the part of the patient to be examined, being arranged on a patient table 4, is situated and wherethrough the "central" X-ray P from the X-ray source 2 to the X-ray detector 3 also extends. Further motions are possible in that the patient table 4 can be displaced in the $z_2$ direction and adjusted in height (in the $z_1$ direction) and in that the entire X-ray device is displaceable in the $z_2$ direction on the rail 81.

Generally speaking, such a C-arm X-ray device is provided with a chain of arms or "links" which are interconnected by way of revolute joints. The first link of the chain is rigidly connected to the building or to a slide so as to be slidable. The last link of the chain, that is, the C-arm, carries the X-ray source as well as the X-ray detector. The revolute joints can be adjusted within given limits and possibly by motor and in a controlled manner. In C-arm X-ray devices of this kind the axes of the revolute joints intersect in the so-called isocenter wherethrough the central X-ray describing the projection direction also extends. The possible movements of the last link of the chain can be described by the trajectory of the X-ray source. Each point on the trajectory corresponds to a possible projection direction. All trajectories extend on a spherical surface whose center is situated at the isocenter. The constraints imposed by the revolute joints, however, limit the feasible trajectories.

Figure 2:
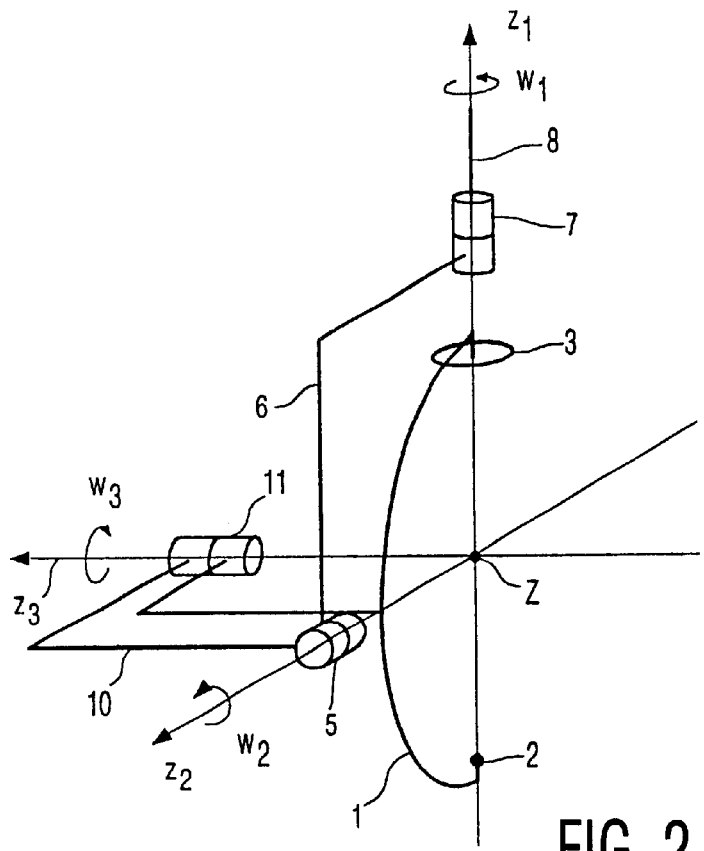
FIG. 2 shows diagrammatically the essential elements of the known X-ray system shown in FIG. 1, FIGS. 3A–3E show sketches of various desirable trajectories.

For the following considerations it is useful to represent the chain of links and revolute joints diagrammatically; this is done in FIG. 2 for the known X-ray device of FIG. 1. Via the joint 7 (ceiling holder) the L-arm 6 is rotatable in an angular range $w_1$, about the $z_1$ axis. The C-arm 1 can be rotated in the angular range $w_2$ about the $z_2$ axis by means of the joint 5 (C-arm holder). The C-arm can be rotated about the $z_3$ axis in the angular range $w_3$ (typically approximately 180°) by means of the joint 11 which is realized by means of circular guide rails in the X-ray device of FIG. 1.

In the known X-ray system the angle $w_3$ can be continuously changed by motor and in a controlled manner. The angle $w_2$ can also be changed by motor, but not continuously. The propeller axis, in this case being the $z_2$ axis, about which the C-arm 1 can rotate via the joint 5 always extends in the horizontal direction because of the construction.

Figure 3A:
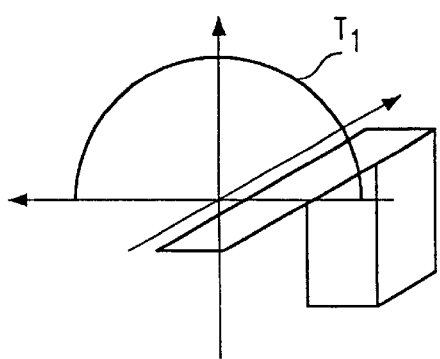
Figure 3B:
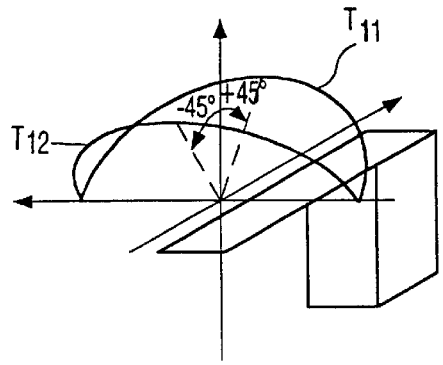
Figure 3C:
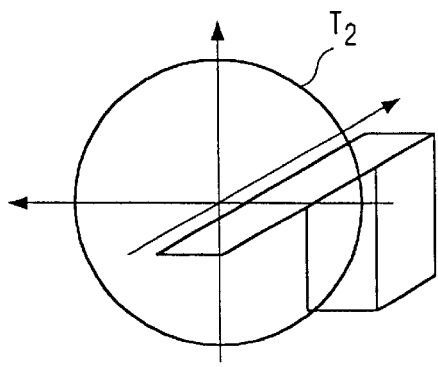
Figure 3D:
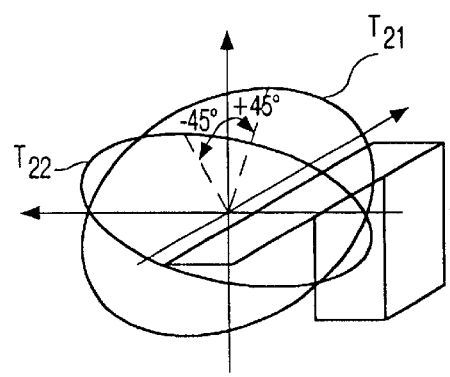
Figure 3E:
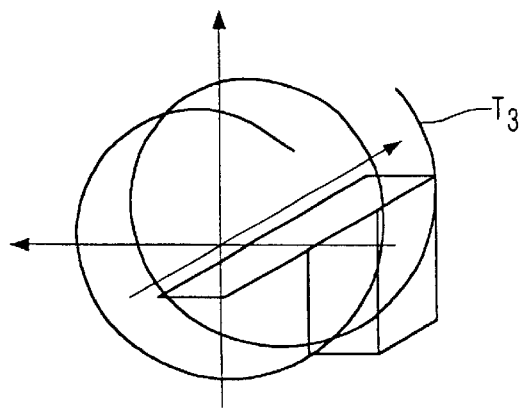

Using the known X-ray device, a semi-circular trajectory $T_1$ as shown in FIG. 3A can be realized. However, such a semi-circle does not yield enough projection directions for a truly exact three-dimensional reconstruction. In theory two tilted, mutually perpendicular semi-circular trajectories $T_{11}$, $T_{12}$ (see FIG. 3B), enabling a better reconstruction, can also be realized. However, in order to maintain an adequate clearance between the patient and the X-ray source or the X-ray detector, in practice the semi-circles can be tilted only through the angle $w_2=\pm 30°$. It would be desirable, however, to realize the trajectories shown in the FIGS. 3C to 3E, that is, trajectories in the form of a full circle (trajectory $T_2$), in the form of two mutually perpendicular full circles (trajectories $T_{21}$ and $T_{22}$) or in the form of a helix (trajectory $T_3$).

Figure 4A:
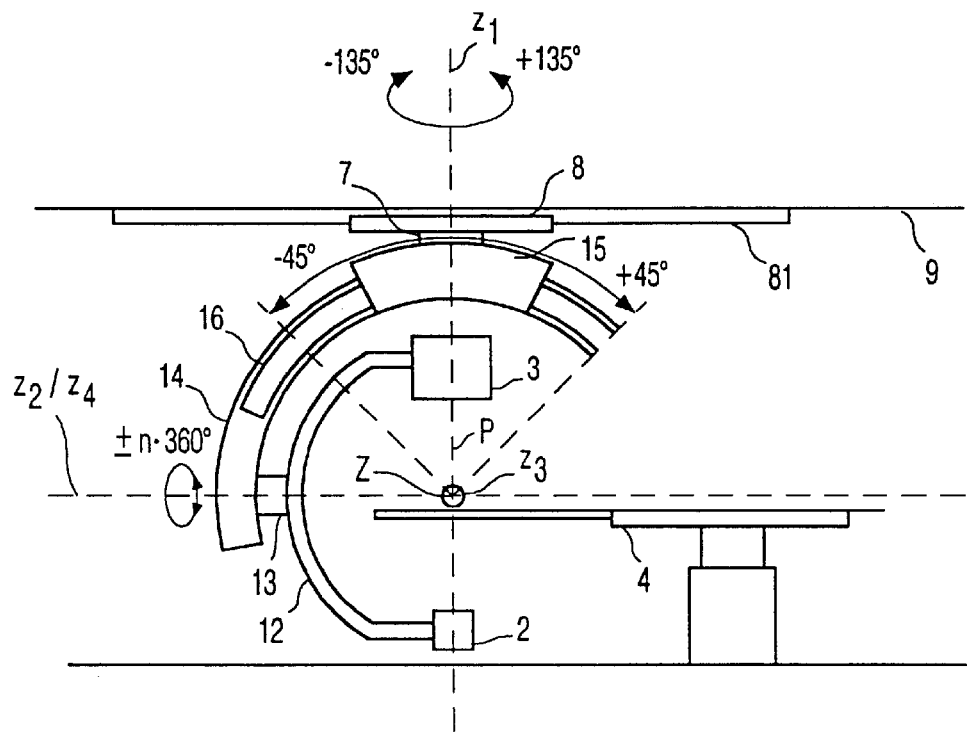
FIGS. 4A, 4B are a side elevation and a plan view, respectively, of a first embodiment of an X-ray device according to the invention.
Figure 4B:
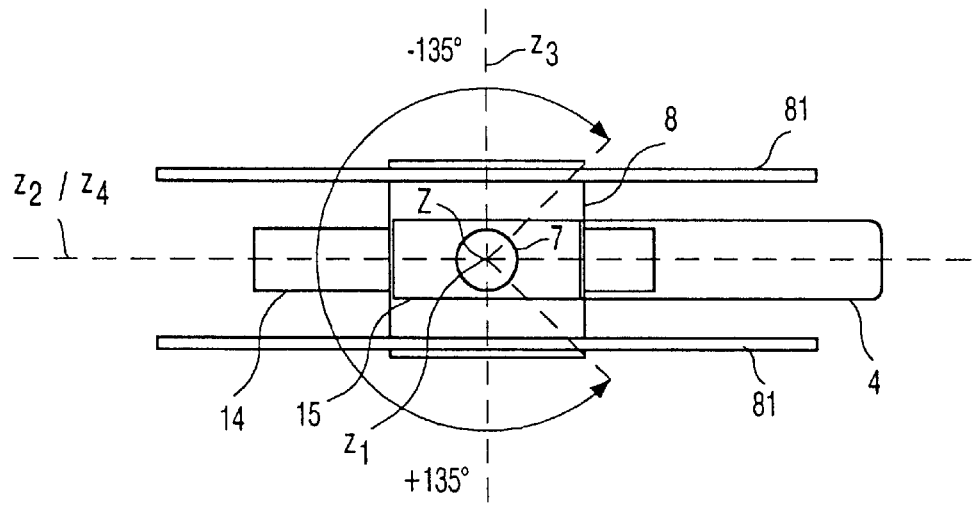

FIGS. 4A, 4B show a first embodiment of an X-ray device according to the invention. Therein, the ceiling holder 7 includes a holding device 15 which itself carries a suspension device 14. The suspension device 14 is of a circular construction and is provided with means 16, for example guide rails or toothed racks, which co-operate with corresponding means in the holding device 15 in such a manner that the suspension device 14 is rotatable about the $z_3$ axis in an angular range of ±45°. The end of the suspension device 14 carries a revolute joint 13 whereto the C-arm 12 with the X-ray source 2 and the X-ray detector 3 is attached.

Figure 5:
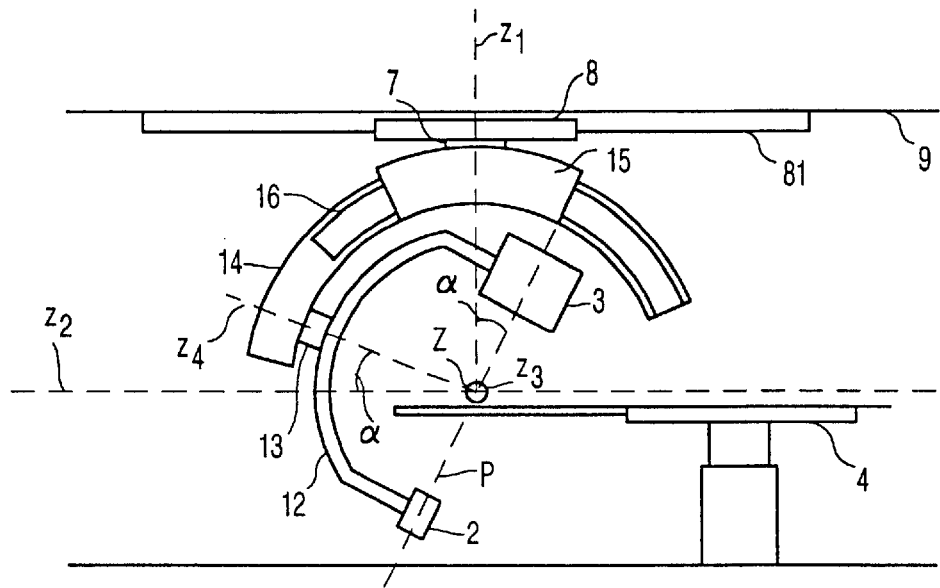
FIG. 5 shows the first embodiment of the X-ray device according to the invention in a different position.

Unlike in the known X-ray device, the rotary motion about the $z_3$ axis is not realized by way of means mounted on the C-arm, but by suitable means provided on the suspension device 14. Because the C-arm is attached to said suspension device 14 by way of the revolute joint 13 so that the suspension device 14 represents the second link in the chain (and not the third link as in the known X-ray device), the position of the propeller axis, referred to hereinafter as the $z_4$ axis, can be changed in all three spatial directions in the X-ray device according to the invention, so also in the $z_1$, direction. In the angular position shown the propeller axis $z_2$ corresponds to the axis $z_2$ extending horizontally through the patient. FIG. 5, however, shows an angular position in which the suspension device 14, and hence also the revolute joint 13 and the C-arm 12, has been rotated through an angle α relative to the $z_2$ axis. The projection direction P has also been rotated through the same angle α relative to the $z_1$ axis.

FIG. 4B is a plan view of the X-ray device according to the invention as shown in FIG. 4A; notably the slide 8 and the rails 81 are clearly shown therein.

Because the C-arm 12 in the X-ray device according to the invention need carry only the X-ray source 2 and the X-ray detector 3, but no means for rotation of the C-arm about the $z_3$ axis, it may be constructed so as to be significantly lighter and trimmer than in the known X-ray device. Therefore, on the one hand angles of rotation of +45° about the $z_3$ axis can be realized. On the other hand, the revolute joint 13 may also be constructed so as to be simpler in such a manner that rotation of the C-arm 12 about the propeller axis $z_4$ is possible through 360° and more. The revolute joint 13 may be provided, for example, with slip rings for the power supply and the transfer of data. Preferably, it is also ensured that the rotation about the propeller axis $z_4$ can take place continuously in a motor-driven and controlled manner. The trajectories shown in the FIGS. 3A to 3E can thus be realized by means of the X-ray device according to the invention. In as far as the rotary motion is possible within a correspondingly shorter period of time, an adequate number of projections for a three-dimensional reconstruction can be obtained also by means of a smaller number of contrast medium injections, possibly by means of a single contrast medium injection.

Figure 6:
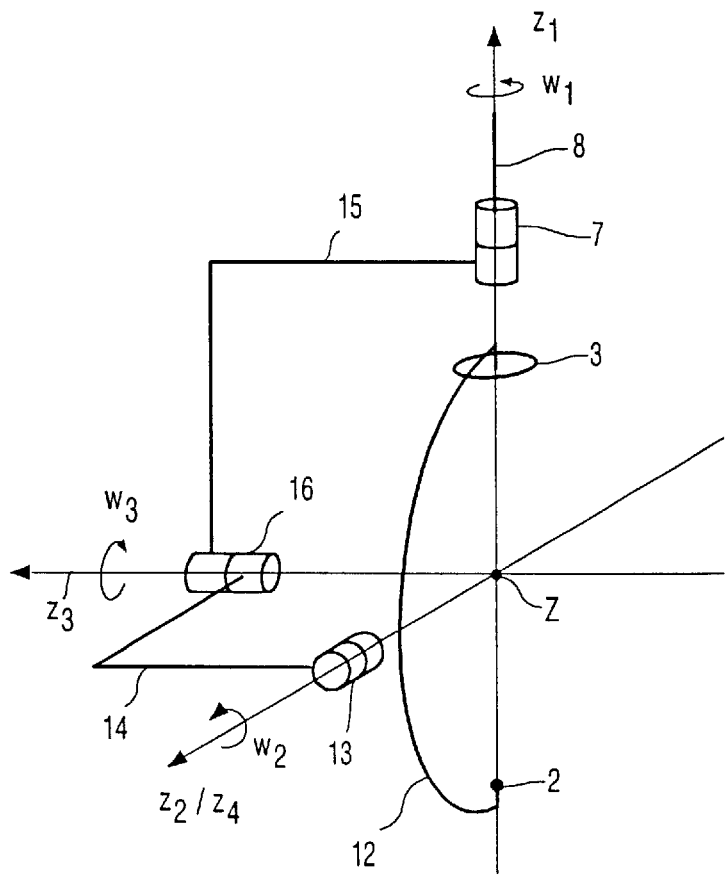
FIG. 6 shows diagrammatically the essential elements of an X-ray device according to the invention.

In order to illustrate the invention, FIG. 6 again shows diagrammatically the essential elements of the X-ray device of FIG. 4A. As can be readily deduced from a comparison with the rendition of FIG. 2, the holding device 15 is now connected to the joint 16 which provides the rotation about the $z_3$ axis and is connected, via the suspension device 14, to the joint 13 whereto the last link in the form of the C-arm 12 is connected so as to be rotatable about the propeller axis $z_4$. In the known X-ray device, however, the L-arm 6 is connected to the joint 5 whereto the C-arm 1 is also connected, so that in the case of a rotation about the $z_2$ axis it is necessary to move not only the C-arm but also the joint 11 and the arm 10.

Figure 7:
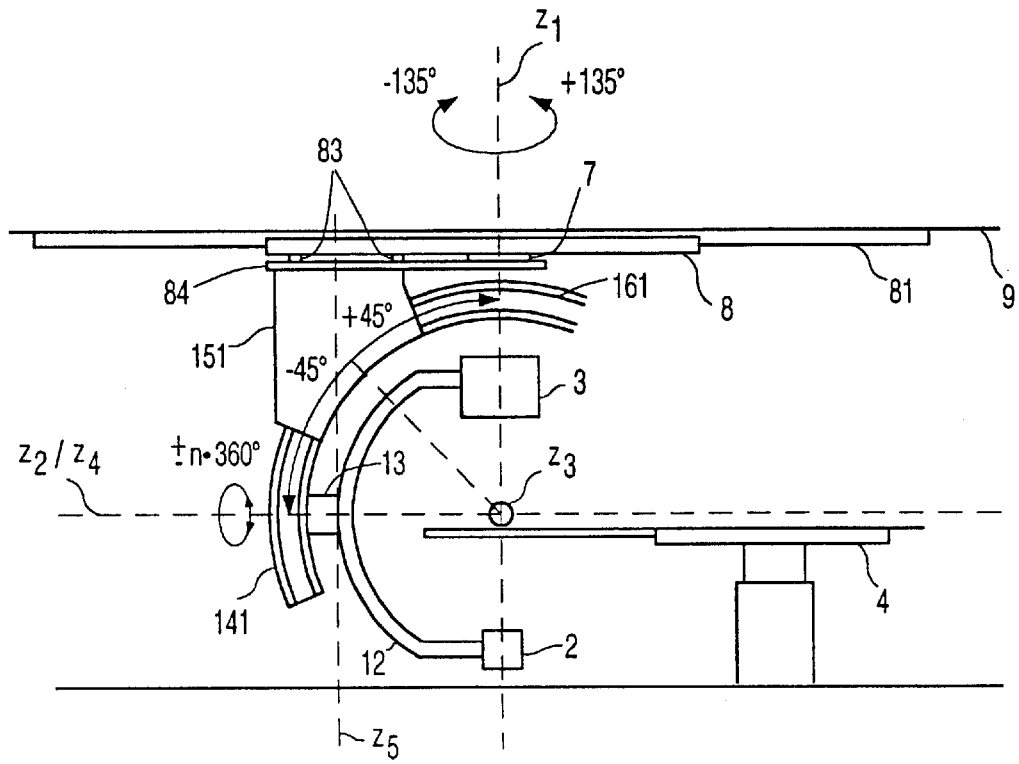
FIG. 7 shows a second embodiment of an X-ray device according to the invention.

FIG. 7 shows an alternative embodiment of an X-ray device according to the invention. Because the holding device 15 is subject to severe one-sided loading in the embodiment shown in FIG. 4A, the holding device 151 in this embodiment is attached to a slide 84 which runs in rails 83 which extend as an arc of a circle about the $z_1$ axis. It is thus achieved that the mass center of the parts of the X-ray device which are connected to the ceiling 9 is situated on a center of gravity axis $z_5$ which extends vertically through the holding device 151 and via which the holding device is indirectly connected (via the slide 84) to the ceiling 9. The suspension device 141 is again constructed as a segment of a circle and provided with guide rails 161 which co-operate with corresponding drive means in the holding device 151.

Figure 8:
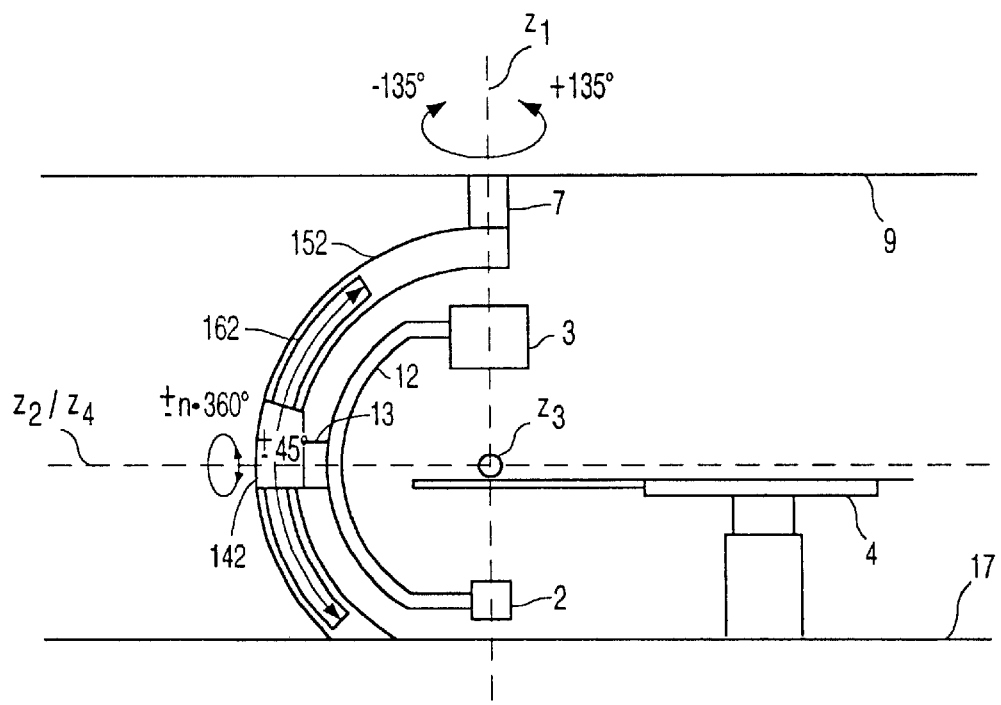
FIG. 8 shows a third embodiment of an X-ray device according to the invention.

FIG. 8 shows another embodiment of the X-ray device according to the invention in which the holding device 152 is constructed practically as a semi-circular segment and is connected, via the joint 7, to the ceiling 9 and, via a joint which is not shown, to the floor 17. The suspension device 142 is now constructed as a component which coaxially encloses the holding device 151 and is moved along the holding device 152 by way of suitable rails 162 so that it can be rotated about the $z_3$ axis.

The embodiments shown are to be considered merely as examples illustrating the invention. Other embodiments are also feasible, their essential feature being that the position of the propeller axis can be changed in all spatial directions. Notably the C-arm may have a different construction, notably a lighter construction. The rounded, circular C-arm is not mandatory either; it may also have a angular shape.

What is claimed is:

1. An X-ray device which includes a C-arm carrying an X-ray source and an X-ray detector, and also includes a suspension device which carries the C-arm via a joint, the X-ray source and the X-ray detector being rotateable about a propeller axis ($z_4$) which extends through the joint, wherein the X-ray device is constructed such that the position of the propeller axis ($z_4$) can be changed in all spatial directions ($z_1$, $z_2$, $z_3$), wherein the suspension device is arranged so as to be rotateable, by means of a holding device, about a vertical axis of rotation ($z_1$) in space.

2. An X-ray device as claimed in claim 1, wherein the suspension device is constructed such that the C-arm and the joint are rotateable about a horizontal axis of rotation ($z_3$) which extends perpendicularly to the propeller axis ($z_4$).

3. An X-ray device as claimed in claim 1, wherein the joint is rigidly connected to the suspension device and the suspension device is connected to a holding device so as to be movable.

4. An X-ray device as claimed in claim 3, wherein the suspension device and the holding device are arranged coaxially relative to one another.

5. An X-ray device as claimed in claim 1, wherein one of the suspension device and the holding device are constructed in the form of an arc of a circle.

6. An X-ray device as claimed in claim 5, wherein one of: the suspension device and the holding device exhibit the same curvature as the C-arm.

7. An X-ray device as claimed in claim 1, wherein the suspension device is attached to a holding device such that the mass center of the suspension device and the C-arm is situated approximately on a vertical center of gravity axis ($z_5$) extending through the holding device.

8. An X-ray device as claimed in claim 1, wherein the joint is constructed as a revolute joint in such a manner that the X-ray source and the X-ray detector can be rotated 360° about the axis of propeller axis ($z_4$) as often as desired.

9. An X-ray device as claimed in claim 1, wherein the joint is constructed such that the rotary motion of the X-ray source and the X-ray detector can be controlled by a motor and in steps.

10. An X-ray device which includes a C-arm carrying an X-ray source and an X-ray detector, and also includes a suspension device which carries the C-arm via a joint, the X-ray source and the X-ray detector being rotateable about a propeller axis ($z_4$) which extends through the joint, wherein the X-ray device is constructed such that the position of the propeller axis ($z_4$) can be changed in all spatial directions ($z_1$, $z_2$, $z_3$), wherein the suspension device is attached to a holding device such that the mass center of the suspension device and the C-arm is situated approximately on a vertical center of gravity axis ($z_5$) extending through the holding device.

* * * * *